(12) United States Patent
Gainor et al.

(10) Patent No.: US 7,479,155 B2
(45) Date of Patent: *Jan. 20, 2009

(54) DEFECT OCCLUDER RELEASE ASSEMBLY AND METHOD

(75) Inventors: John P. Gainor, White Bear Township, MN (US); Brian L. Dukart, Brooklyn Park, MN (US); Darren L. Wegner, St. Paul, MN (US)

(73) Assignee: EV3 Endovascular, Inc., Plymouth, MN (US)

( * ) Notice: Subject to any disclaimer, the term of this patent is extended or adjusted under 35 U.S.C. 154(b) by 1241 days.

This patent is subject to a terminal disclaimer.

(21) Appl. No.: 10/227,773

(22) Filed: Aug. 26, 2002

(65) Prior Publication Data

US 2002/0198563 A1 Dec. 26, 2002

Related U.S. Application Data

(63) Continuation of application No. 09/628,211, filed on Jul. 28, 2000, now Pat. No. 6,440,152.

(51) Int. Cl.
*A61B 17/08* (2006.01)
*A61D 1/00* (2006.01)

(52) U.S. Cl. ...................................... 606/213
(58) Field of Classification Search ................ 606/213; 623/23.72

See application file for complete search history.

(56) References Cited

U.S. PATENT DOCUMENTS 3,124,136 A 3/1964 Usher
3,874,388 A 4/1975 King et al. .............. 128/334 R (Continued)

FOREIGN PATENT DOCUMENTS

EP 0 362 113 4/1990

(Continued)

OTHER PUBLICATIONS

Ruiz, C.E. et. Al., "The Puncture Technique: A New Method for Transcatheter Closure of Patent Foramen Ovale", Cath. And Cardiovasc. Interv. 53:369-372 (2001).

(Continued)

*Primary Examiner*—Todd E Manahan
*Assistant Examiner*—Christina D Gettman
(74) *Attorney, Agent, or Firm*—Knobbe, Martens, Olson & Bear, LLP

(57) ABSTRACT

A release assembly is provided to aid the reversible and repositionable deployment of a defect occluder. The release assembly includes an occluder tether having a distal portion comprising at least one suture loop, and a snare structure having a distal portion comprising a snare element. The at least one suture loop is receivable through at least a portion of the defect occluder, and reversibly looped over an anchor element so as to permit reversible collapse the defect occluder for selective ingress and egress from a delivery catheter. The snare element is reversibly engageable with the anchor element so as to reversibly retain the at least one suture loop upon the anchor element, and thereby hold the defect occluder in a posture for reversible free-floating tethered deployment in a defect while being observable in a final position prior to release.

27 Claims, 1 Drawing Sheet

U.S. PATENT DOCUMENTS

| | | | |
|---|---|---|---|
| 4,007,743 A | 2/1977 | Blake | 128/334 R |
| 4,781,177 A | 11/1988 | Lebigot | |
| 4,836,204 A | 6/1989 | Landymore et al. | 128/334 R |
| 4,917,089 A | 4/1990 | Sideris | 606/215 |
| 5,021,059 A | 6/1991 | Kensey et al. | |
| 5,108,420 A | 4/1992 | Marks | 606/213 |
| 5,171,259 A | 12/1992 | Inoue | 606/213 |
| 5,192,301 A | 3/1993 | Kamiya et al. | 606/213 |
| 5,254,133 A | 10/1993 | Seid | 606/215 |
| 5,258,000 A | 11/1993 | Gianturco | 606/151 |
| 5,284,488 A | 2/1994 | Sideris | 606/213 |
| 5,334,217 A * | 8/1994 | Das | 606/213 |
| 5,342,393 A | 8/1994 | Stack | 606/213 |
| 5,350,399 A | 9/1994 | Erlebacher et al. | 606/213 |
| 5,356,432 A | 10/1994 | Rutkow et al. | |
| 5,397,331 A | 3/1995 | Himpens et al. | 606/151 |
| 5,425,744 A | 6/1995 | Fagan et al. | 606/213 |
| 5,433,727 A | 7/1995 | Sideris | 606/213 |
| 5,451,235 A | 9/1995 | Lock et al. | 606/213 |
| 5,486,193 A | 1/1996 | Bourne et al. | |
| 5,507,811 A | 4/1996 | Koike et al. | 623/11 |
| 5,578,045 A | 11/1996 | Das | 606/151 |
| 5,634,936 A | 6/1997 | Linden et al. | |
| 5,643,317 A | 7/1997 | Pavcnik et al. | 606/213 |
| 5,662,681 A | 9/1997 | Nash et al. | 606/213 |
| 5,709,707 A | 1/1998 | Lock et al. | 606/213 |
| 5,725,552 A | 3/1998 | Kotula et al. | 606/213 |
| 5,733,294 A | 3/1998 | Forber et al. | 606/151 |
| 5,741,297 A | 4/1998 | Simon | 606/213 |
| 5,792,179 A | 8/1998 | Sideris | |
| 5,797,960 A | 8/1998 | Stevens et al. | |
| 5,823,956 A | 10/1998 | Roth et al. | |
| 5,829,447 A | 11/1998 | Stevens et al. | |
| 5,846,261 A | 12/1998 | Kotula et al. | 606/213 |
| 5,853,422 A | 12/1998 | Huebsch et al. | 606/213 |
| 5,855,614 A | 1/1999 | Stevens et al. | |
| 5,860,948 A | 1/1999 | Buscemi | |
| 5,861,003 A | 1/1999 | Latson et al. | 606/213 |
| 5,879,366 A | 3/1999 | Shaw et al. | 606/213 |
| 5,904,703 A | 5/1999 | Gilson | |
| 5,919,200 A | 7/1999 | Stambaugh et al. | |
| 5,944,738 A | 8/1999 | Amplatz et al. | 606/213 |
| 5,947,997 A | 9/1999 | Pavcnik et al. | 606/213 |
| 5,976,174 A | 11/1999 | Ruiz | 606/213 |
| 6,024,756 A | 2/2000 | Huebsch et al. | 606/213 |
| 6,059,823 A | 5/2000 | Holman et al. | |
| 6,077,281 A | 6/2000 | Das | |
| 6,077,291 A | 6/2000 | Das | |
| 6,079,414 A | 6/2000 | Roth | |
| 6,080,182 A | 6/2000 | Shaw et al. | |
| 6,087,552 A | 7/2000 | Gregory | |
| 6,096,052 A | 8/2000 | Callister et al. | |
| 6,106,532 A | 8/2000 | Koike et al. | |
| 6,110,212 A | 8/2000 | Gregory | |
| 6,123,715 A | 9/2000 | Amplatz | |
| 6,152,144 A | 11/2000 | Lesh et al. | |
| 6,156,055 A | 12/2000 | Ravenscroft | |
| 6,171,329 B1 | 1/2001 | Shaw et al. | 606/213 |
| 6,174,322 B1 | 1/2001 | Schneidt | |
| 6,190,400 B1 | 2/2001 | Van De Moer et al. | |
| 6,200,336 B1 | 3/2001 | Pavcnik et al. | |
| 6,206,895 B1 | 3/2001 | Levinson | |
| 6,206,907 B1 | 3/2001 | Marino et al. | |
| 6,210,338 B1 | 4/2001 | Afremov et al. | |
| 6,214,029 B1 | 4/2001 | Thill et al. | 606/213 |
| 6,221,092 B1 | 4/2001 | Koike et al. | |
| 6,231,561 B1 | 5/2001 | Frazier et al. | |
| 6,238,416 B1 | 5/2001 | Sideris | |
| 6,245,079 B1 | 6/2001 | Nobles et al. | |
| 6,270,515 B1 | 8/2001 | Linden et al. | |
| 6,277,140 B2 | 8/2001 | Ginn et al. | |
| 6,280,460 B1 | 8/2001 | Bolduc et al. | |
| 6,290,674 B1 | 9/2001 | Roue et al. | |
| 6,299,597 B1 | 10/2001 | Buscemi et al. | |
| 6,306,177 B1 | 10/2001 | Felt et al. | |
| 6,312,446 B1 | 11/2001 | Huebsch et al. | |
| 6,319,263 B1 | 11/2001 | Levinson | |
| 6,319,276 B1 | 11/2001 | Holman et al. | |
| 6,328,727 B1 | 12/2001 | Frazier et al. | |
| 6,334,864 B1 | 1/2002 | Amplatz et al. | |
| 6,346,074 B1 | 2/2002 | Roth | |
| 6,355,052 B1 | 3/2002 | Neuss et al. | |
| 6,375,671 B1 | 4/2002 | Kobayashi et al. | |
| 6,391,048 B1 | 5/2002 | Ginn et al. | |
| 6,440,152 B1 | 8/2002 | Gainor et al. | |
| 6,458,100 B2 | 10/2002 | Roue et al. | |
| 6,461,364 B1 | 10/2002 | Ginn et al. | |
| 6,468,303 B1 | 10/2002 | Amplatz et al. | |
| 6,551,303 B1 | 4/2003 | Van Tassel et al. | |
| 6,551,344 B2 | 4/2003 | Thill | |
| 6,596,014 B2 | 7/2003 | Levinson et al. | |
| 6,626,917 B1 | 9/2003 | Craig | |
| 6,635,066 B2 | 10/2003 | Tanner et al. | |
| 6,645,225 B1 | 11/2003 | Atkinson | |
| 6,776,784 B2 | 8/2004 | Ginn | |
| 7,288,105 B2 | 10/2007 | Oman et al. | |
| 2001/0014800 A1 | 8/2001 | Frazier et al. | |
| 2001/0021872 A1 | 9/2001 | Bailey et al. | |
| 2001/0023332 A1 | 9/2001 | Hahnen | |
| 2001/0031973 A1 | 10/2001 | Nobles et al. | |
| 2001/0039434 A1 | 11/2001 | Frazier et al. | |
| 2001/0039435 A1 | 11/2001 | Roue et al. | |
| 2001/0039436 A1 | 11/2001 | Frazier et al. | |
| 2001/0039450 A1 | 11/2001 | Pavcnik et al. | |
| 2001/0041914 A1 | 11/2001 | Frazier et al. | |
| 2001/0041915 A1 | 11/2001 | Roue et al. | |
| 2001/0049292 A1 | 12/2001 | Frazier et al. | |
| 2002/0055767 A1 | 5/2002 | Forde et al. | |
| 2002/0068950 A1 | 6/2002 | Corcoran et al. | |
| 2002/0169475 A1 | 11/2002 | Gainor et al. | |
| 2002/0183787 A1 | 12/2002 | Wahr et al. | 606/213 |
| 2003/0023262 A1 | 1/2003 | Welch | 606/194 |
| 2003/0144694 A1 | 7/2003 | Chanduszko et al. | |
| 2003/0191495 A1 | 10/2003 | Ryan et al. | |
| 2003/0195530 A1 | 10/2003 | Thill | |
| 2003/0220667 A1 | 11/2003 | van der Burg et al. | |
| 2003/0225421 A1 | 12/2003 | Peavey et al. | |
| 2004/0073242 A1 | 4/2004 | Chanduszko | |
| 2004/0092973 A1 | 5/2004 | Chanduszko et al. | |
| 2004/0098121 A1 | 5/2004 | Opolski | |
| 2004/0220596 A1 | 11/2004 | Frazier et al. | |
| 2004/0243122 A1 | 12/2004 | Auth et al. | |
| 2004/0267191 A1 | 12/2004 | Gifford, III et al. | |
| 2005/0033327 A1 | 2/2005 | Gainor et al. | |
| 2005/0119675 A1 | 6/2005 | Adams et al. | |
| 2005/0187568 A1 | 8/2005 | Klenk et al. | |
| 2005/0192626 A1 | 9/2005 | Widomski et al. | |
| 2005/0251201 A1 | 11/2005 | Roue et al. | |
| 2007/0106327 A1 | 5/2007 | Thill et al. | |
| 2007/0112382 A1 | 5/2007 | Thill et al. | |

FOREIGN PATENT DOCUMENTS

| | | |
|---|---|---|
| EP | 0 474 887 A | 3/1992 |
| EP | 0 655 222 B1 | 6/1998 |
| EP | 0 541 063 B1 | 9/1998 |
| EP | 0 876 793 A2 | 11/1998 |
| EP | 0 920 842 A1 | 6/1999 |
| EP | 1 046 375 A1 | 10/2000 |
| GB | 2 269 321 | 2/1994 |
| JP | 3-286752 | 12/1991 |
| JP | 7171173 | 7/1995 |
| JP | 8141070 | 6/1996 |
| JP | 8196623 | 8/1996 |

| | | |
|---|---|---|
| WO | WO 90/14796 | 12/1990 |
| WO | WO 93/13712 | 7/1993 |
| WO | WO 95/28885 A | 11/1995 |
| WO | WO 96/32882 A | 10/1996 |
| WO | WO 97/41779 | 11/1997 |
| WO | WO 97/42878 | 11/1997 |
| WO | WO 98/08462 | 3/1998 |
| WO | WO 99/07289 | 2/1999 |
| WO | WO 99/18862 | 4/1999 |
| WO | WO 99/18864 | 4/1999 |
| WO | WO 99/18871 | 4/1999 |
| WO | WO 99/38454 | 8/1999 |
| WO | WO 99 40849 | 8/1999 |
| WO | WO 99/56376 | 9/2000 |
| WO | WO 00 69365 | 11/2000 |
| WO | WO 01 17435 | 3/2001 |
| WO | WO 01/21246 | 3/2001 |
| WO | WO 02/32496 | 4/2002 |
| WO | WO 02/38051 | 5/2002 |
| WO | WO 02/098298 A1 | 12/2002 |

OTHER PUBLICATIONS

Sociedade Brasileira de Cardiologia at http://www.cardiol.br/esquina/temas/2000/jan/030.htm, *Transcatheter Closure of Atrial-Septal Defects and Patent Foramen ovale in Adults: Optimal Anatomic Adaptation of Occlusion Device* by H.W. Hoepp, M.D. et al., Am Heart J 138(5):941-949, 1999. © 1999 Mosby-Year Book, Inc.
Notice of Allowance dated Jan. 30, 2008 in U.S. Appl. No. 10/930,321.

* cited by examiner

DEFECT OCCLUDER RELEASE ASSEMBLY AND METHOD

This application is a continuation of U.S. application Ser. No. 09/628,211, filed Jul. 28, 2000, now U.S. Pat. No. 6,440,152.

TECHNICAL FIELD

The present invention generally relates to devices for occluding septal defects or shunts in the heart or the vascular system, and more particularly to a component of an interventional transcatheter delivery system for holding a defect occluder in a posture for reversible free-floating tethered deployment from a catheter for occluding a septal defect or the like, and an attendant method.

BACKGROUND OF INVENTION

The term "septal defect" generally refers to a perforation or other type hole (i.e., a defect) which passes through a thin wall of muscle or other tissue (i.e., a septum) which divides or separates "areas" within the body. Such defects can occur, either congenitally or by acquisition, between chambers of the heart (i.e., atrium or ventricle) or the great vessels (interatrial and interventricular septal defects or patent ductus arteriosus and aortico-pulminatry window respectively), causing shunting of blood through the opening.

Atrial septal defects were initially corrected by open heart surgery which required the surgeon to open the chest of a patient and bypass the heart temporarily (e.g., by means of a mechanical heart or a "heart-lung machine"). The surgeon would then physically cut into the heart and suture small defects closed. In the case of larger defects, a patch of a biologically compatible material would be sewn onto the septum to cover (i.e., "patch") the defect. Balloon catheters, similar to that disclosed by Landymore et al. in U.S. Pat. No. 4,836,204, have been used by physicians to temporarily occlude septal defects, as a stabilizing measure, prior to implementation of corrective open heart surgical techniques.

To overcome limitations of surgical closure, a variety of interventional transcatheter closure techniques have been attempted. In such techniques, an occluding device is delivered through a catheter to the septal defect site. Once the closure device is positioned adjacent the defect, it must be attached to the rest of the septum in a manner which permits it to effectively block the passage of blood through the defect.

One such early closure device, U.S. Pat. No. 3,874,388 (King et al.), includes a pair of complex mechanical umbrellas, each having a plurality of arms extending radially from a central hub. The hubs of the two umbrellas are mechanically connected to one another and each umbrella includes a fabric covering over the arms, much like a common umbrella. The ends of each arm are provided with barbs which are anchored into the septum to hold the occluder in place. The complex umbrellas prove rather difficult to unfold after passage through a catheter, requiring an array of cables to deploy the arms. This makes proper placement of the device difficult, and the barbs on the arms prevent retraction or repositioning of the device once it is in place.

Although much progress has been made in the field since the King et al. device, heretofore known defect occluding systems, whether they be of a traditional atrial umbrella style (e.g., the ClamShell Septal Umbrella (ClamShell I, C.R. Bard, Inc.), the CardioSEAL device (Nitinol Medical Technologies, Inc.), the Sideris Buttoned Occluder (Sideris, U.S. Pat. No. 4,917,089), or the ASD Occlusion System (ASDOS, Dr. Osypka GmbH, Grenzach-Wyhlen, Germany), or other emerging plug style (e.g., The Monodisk System (Pavenik et al., U.S. Pat. No. 5,643,317), Angel Wings (Das, U.S. Pat. No. 5,578,045), the Amplatzer® Septal Occluder, or the HELEX Septal Occluder (W.L. Gore & Associates, Inc.), all suffer from a variety of common shortcomings.

These, and other such devices, generally rely on the caudal and cranial ends of the device being larger than the opening of the defect itself to physically trap the device across the opening. To accommodate transcatheter delivery techniques, the resulting device configurations have become unduly mechanical in nature, often including multiple components (e.g., ASDOS) and/or requiring the sequential delivery of device components, as well as the use of loading jigs (e.g., ASDOS, CardioSEAL) to prepare the device for insertion. Furthermore, many of these devices require assembly across the defect post delivery (e.g., ASDOS), thereby increasing the complexity of the transcatheter equipment, and delivery process, as for instance, by requiring two separate catheter entry points (e.g., ASDOS).

Further still, and of primary importance, heretofore known defect occluders do not optimally conform to the size (i.e., contour, dimensions and/or geometry) of the septal defect. Such devices therefore require great care in placement to ensure that the closure members entirely cover the defect. Because previously known devices typically use expanding frames to support the closure members that can straddle the opening of the defect, or otherwise become caught, complications may arise during implantation of such devices.

Generally, a great deal of remote manipulation and repositioning is required for proper device deployment because heretofore known defect occluder systems hold or retain the occluder in such a way that the device cannot be observed in its final, fully expanded position within the defect until the device is completely released. Extensive remote manipulation, such as by applying tension to one or more cables in order to deploy the arms of an umbrella, for instance, or to anchor the device in place, not only increases the difficulty of the procedure, but tends to increase the likelihood that the device will be improperly deployed, or suffer material fatigue leading to device strut fracture, a fundamental and well documented problem of the aforementioned umbrella type devices. Further still, the likelihood of retrieval of such devices post deployment is great, and in some cases retrieval is required so as to effectively occlude the defect and minimize the risk of embolization.

Occluder systems generally have either a single "hard point" connection (i.e., the occluder is held for deployment by a substantially rigid "hard point" connection until final release thereof within a defect), or a dual point connection, namely a hard point connection in combination with a "soft" secondary release mechanism (e.g., a release cord or suture used to provide emergency retrieval post hard point release). With the single hard point connection, a cyclical flexing of the occluder is possible therewith, however, once the hard point is disengaged from the occluder, further adjustment and retrieval is no longer possible.

For example, the Amplatzer® and ASDOS single hard point systems push the occluder from the catheter into the defect using an externally threaded rod (i.e., torquer catheter) that mates with a threaded nut, or the like, integral to the occluder, with release of the device thereafter once the occluder is adequately seated in the defect. A major shortcoming of this method is that the position of the catheter tip in the heart in relation to the fully deployed occluder usually pulls the occluder into an unintended, and unnatural position. This distorts the septum of the heart, and the physician must trust that upon release of the occluder from the delivery system, the septum will return to a natural position and the occluder will adequately seal the defect. The single hard point connection does not permit the physician to observe the occluder as it would sit naturally in the heart until it is released.

The dual point connection, which specifically addressed the shortcomings of the single hard point connection, provides a mechanism by which the occluder may be emergently retrieved in the case of mis-deployment after hard point release. The dual point CardioSEAL and HELEX systems permit the physician to better observe the occluder in a more "natural" condition or state, having previously disengaged the occluder from the single hard point connection, thereby effectively minimizing potential cardiac distortion. However, due to the nature of the soft point connection, no effective repositioning may be effectuated once the hard point connection has been disengaged without fear of damaging the occluder and thereby causing malfunction: only retrieval is possible should mis-deployment of the occluder be suspected. A further disadvantage to this method of occluder attachment is that occluder redeployment is not possible: having disengaged the hard point "control" connection, redeployment, in addition to repositioning, is no longer possible, with occluder retrieval via the soft point connection typically destroying the device. The soft point attachment is generally released by cutting the suture or cord at the rear of the delivery system, and drawing the full length of the suture from the occluder and through the entire delivery system—a procedure which effectively opens a fluid pathway from the rear of the delivery system into the area of the defect, especially of concern when occluding an atrial or ventricle defect, thereby creating attendant risks with such release arrangement and procedure.

It is, therefore, advantageous to provide a defect occluder system capable of reversibly retaining an occluder so as to be observable in its final position prior to release. More particularly, it is highly desirable to provide a delivery system release assembly which allows the device to free float in the defect, while maintaining the ability to reposition and or retrieve it, at any time prior to final release, without implicating occluder integrity. Further still, it is desirable to provide in a defect occluder delivery system a soft occluder release accomplished with reduced attendant patient risk, such as the elimination of problems associated with opening the fluid pathway from the rear of the delivery system into the heart.

SUMMARY OF THE INVENTION

A release assembly is provided to aid the reversible and repositionable deployment of a defect occluder. The release assembly includes an occluder tether having a distal portion comprising at least one suture loop, and a snare structure having a distal portion comprising a snare element. The at least one suture loop is receivable through at least a portion of the defect occluder, and reversibly looped over an anchor element so as to permit reversible collapse the defect occluder for selective ingress and egress from a delivery catheter. The snare element is reversibly engageable with the anchor element so as to reversibly retain the at least one suture loop upon the anchor element, and thereby hold the defect occluder in a posture for reversible free-floating tethered deployment in a defect while being observable in a final position prior to release.

More specific features and advantages obtained in view of those features will become apparent with reference to the drawing figures and DETAILED DESCRIPTION OF THE INVENTION.

DETAILED DESCRIPTION OF THE INVENTION

Release assemblies are generally considered to be a component of an occluder delivery system, such systems being typically characterized as including a delivery catheter for containing or housing an occluder pre-deployment, and a "pusher tube," having at least one lumen for receiving an occluder control mechanism, for moving the occluder through the delivery catheter to the septal defect. These, as well as other occluder delivery systems are described in the literature, and are well know to those of skill in the art.

Figure 1:
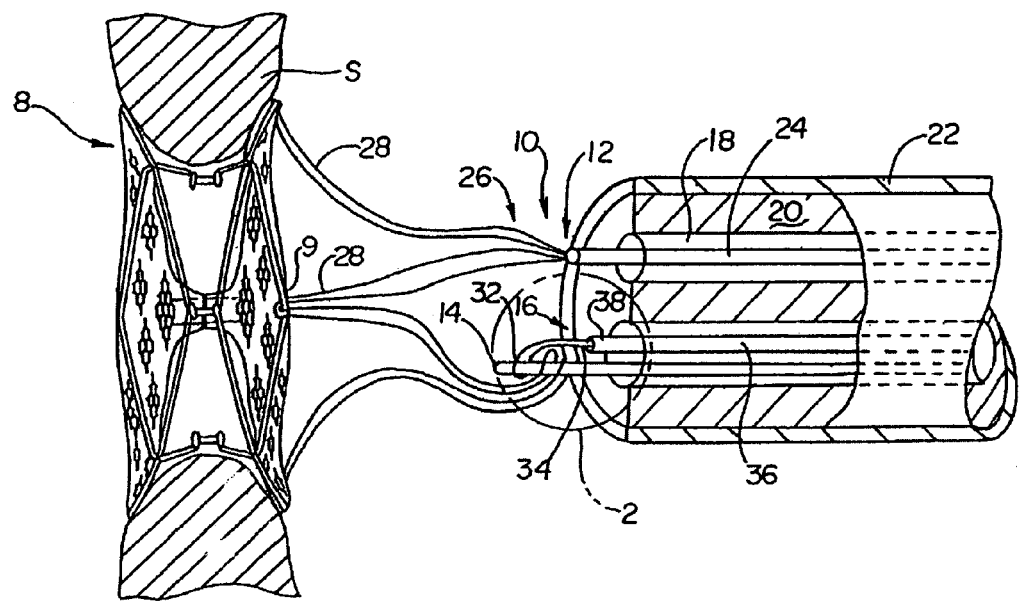
FIG. 1 is a side elevational view of a deployed septal defect occluder tethered to the release assembly of the present invention, shown in a sectional side view, with parts broken away to show underlying detail; and, FIG. 2 is a detailed view of area shown in FIG. 1, illustrating the pin wire and snare structure of the present invention, particularly showing retention of suture loops on the pin wire, and the occluder thereby, by a snare loop.

Referring to FIG. 1, a septal defect closure device 8 is shown in a reversible free-floating tethered deployment relative a septum S (e.g., an atrial septum) so as to effectively conform and block a defect, thereby preventing the flow of blood through the atrial septum to the adjoining chambers. The septal defect closure device need not be of the style shown, or any particular or preferred style, as all are readily deployable, or at a minimum easily adapted for deployment by those of skill in the art, using the release assembly of the subject invention. The release assembly 10 of the present invention generally includes an occluder tether 12, an anchor element 14, and a snare structure 16, each of which being receivable in the lumens 18 of a multi-lumen pushing tube 20 which is disposed within a delivery catheter 22. A discussion of these elements, their components, and the interrelationships therebetween follows.

Figure 2:
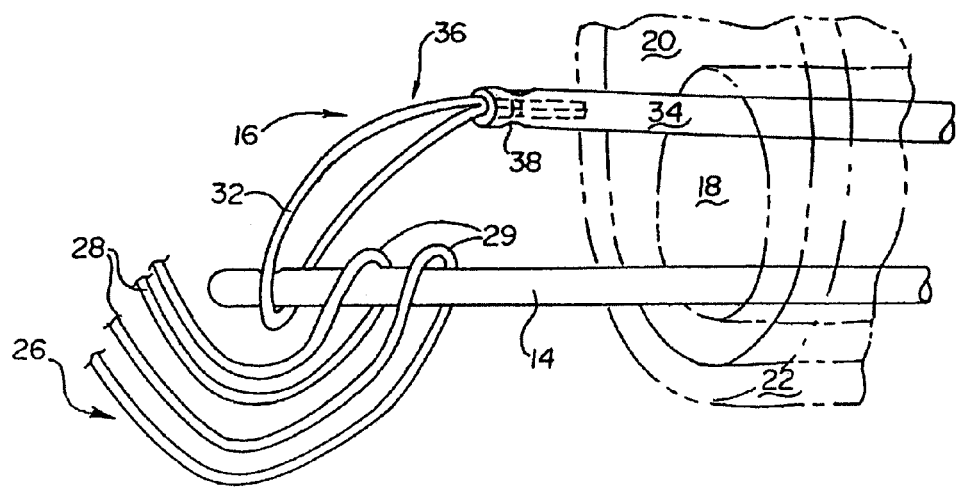

Referring now to FIGS. 1 and 2, the occluder tether 12, reversibly extendible from a distal end of a first lumen, generally has proximal 24 and distal 26 portions, the distal portion 26 (i.e., component nearest the occluder 8) comprising at least one suture loop 28 receivable through at least a portion of the occluder 8. The at least one suture loop 28 is reversibly looped over the anchor element 14 so as to permit reversible collapse of the occluder 8 for selective ingress and egress from the delivery catheter 22. The snare structure 16, which is extendible from a distal end of a second lumen, has a distal portion comprising a snare element 32. The snare element 32 is received by, or otherwise cooperatively engaged with/to, the anchor element 14, which may be disposed within its own lumen (i.e., third lumen, not shown), or within the second lumen, as shown in FIG. 1, so as to reversibly retain (e.g., by obstructing) the at least one suture loop 28 upon the anchor element 14. In this way the snare element 32 effectively "holds" the defect occluder 8 in a posture for reversible free-floating tethered deployment in a defect while being observable in a final position prior to release.

In the embodiment illustrated, the occluder tether 12 is shown having two suture loops 28, the number of suture loops being dictated by application specific variables (e.g., nature of the defect, style of selected occluder, etc.). Generally, the at least one suture loop 28 is receivable through, or otherwise arranged to cooperate with, portions of the occluder 8 for manipulation during deployment. In FIG. 1, the dual suture loops 28 are shown received in (i.e. threaded through) eyelets 9 of an occluder 8. The "free" ends 24 of the dual loops 28 (i.e., loop crotches) are reversibly received about the anchor element 14 to controlingly hold the occluder 8.

The occluder tether 12 may be of unitary or composite construction or composition. The proximal portion 24 of the occluder tether 12 may be constructed of nitinol, or of any type of metal or plastic that demonstrates good flexibility and kink resistance, whereas the distal portion 26, more particularly the suture loops 28 themselves, may be constructed of stranded nitinol, stranded polyester, straight nitinol, spring temper stainless steel, braided silk, braided polyester, braided nylon, or polyester or nylon monofilament, or any other material that demonstrates good kink resistance, flexibility, and low stretch. Although the tether portions 24 and 26 may be discrete elements, joined as will be later discussed with respect to the snare structure 16, it is only necessary that the suture loops 28 extend from the proximal portion 24 of the tether 12 such that the tether structure 12 possesses sufficient tensile strength for occluder manipulation and retrieval.

The snare structure 16, like the occluder tether 12, has proximal 34 and distal 36 portions, and may be of unitary or composite construction or composition. The proximal portion 34 may be made of nitinol, or of any type of material that demonstrates good flexibility and kink resistance. As shown in the figures, the snare element 32 is preferably a loop, although functional equivalents and alternatives to the snare loop are contemplated, and include, but are not limited to, balls, disks, or other structures that retain the suture loops 28 on the anchor element 14 (i.e., keep the suture loops 28 from inadvertent or unintended release) prior to selective release of the occluder. In the form of a loop, the snare element 32 may be made of stranded nitinol, straight nitinol, braided polyester, braided nylon, braided silk, polyester or nylon monofilament, or any other material that demonstrates good kink resistance and flexibility.

With particular reference to FIG. 2, the snare structure portions 34 and 36 are indicated as being united discrete elements. The snare loop 32 has an end thereof received in/at an end of the proximal portion 34 of the snare structure 16 (i.e., the distal end surface thereof), the interface of the proximal 34 and distal 36 portions of the snare structure 16 being characterized by a crimp 38 which secures the portions 34 and 36 to each other, and thereby forms a unitary snare structure 16. Other known methods of joining the snare structure portions 34 and 36 are contemplated, in addition to an integral fabrication of the snare structure 16 (e.g., unitary construction).

In the form of a ball, the snare element 32 is preferably welded on the end of the proximal portion 34 of the snare structure 16, and is constructed of identical, or at least compatible, construction materials. In the form of a disk, the snare element 32 is preferably welded, crimped or otherwise affixed onto the end of the proximal portion 34 of the snare structure 16, but may be attached by any method that provides sufficient tensile strength for retaining the suture loops 28 upon the anchor element 14. The material of the disk may be any material that has structural rigidity and is readily affixable to the material of the proximal portion 34 of the snare structure 16.

The anchor element 14 is preferably a pin wire. The pin wire may be made of nitinol, or of any type of metal or plastic that demonstrates a combination of good flexibility to avoid excessive stiffening of the catheter, and structural strength to prevent premature suture loop release caused by wire buckling. The pin wire 14 receives the suture loops 28 and the snare element 32 so as to anchor the occluder during deployment, placement, and adjustment procedures.

The preferred configuration of the release assembly 10 is to pass the occluder tether 12 through one lumen 18 of a double lumen pusher tube 20, and pass both the snare structure 16 and the anchor element 14 through the other lumen of the same pusher tube 20. The double lumen tubing 20 is sized such that it fits inside the lumen of the outer catheter 22 of the delivery system. The suture loops 28 are passed through the eyelets 9, or equivalent tether receiving structure(s), of the occluder 8, and the loop ends 29 are hooked over the free end of the pin wire 14. The loop 32 of the snare structure 16 is then hooked over the pin wire 14, distal to the suture loops 28, with the pin wire 14 advanceable in relation to the snare loop 32 in order to prevent the snare loop 32 from sliding off the pin wire 14. To release the suture loops 28, the pin wire 14 is retracted in relation to the snare loop 32, thereby liberating the suture loops 28 from the pin wire 14. Thereafter, retraction of the occluder tether 12, in relation to the occluder 8, draws the suture loops 28 out of the eyelets 9 of the occluder 8, thereby releasing the device.

As to the preferred characteristics of the release assembly components, the proximal portion of the tether is approximately 0.029" diameter nitinol wire of approximately 47.25" (120 centimeters) in length. A hole or crater is present in the end (i.e., the distal end surface of the proximal tether portion) that is about 0.100" deep and approximately 0.017" in diameter. This hole receives the ends of the two suture loops that are crimped into place, the suture loops being constructed of stranded nitinol wire with a diameter of approximately 0.006". The suture loops are of a length sufficient to be threaded through the eyelets of an occluder so that the device is allowed to rest in a fully deployed position while the suture loops remain substantially slack (i.e., permit free-floating deployment of the occluder into the defect).

The proximal portion of the snare structure is a nitinol wire having a diameter of about 0.029" and a length of approximately 47.25". Like the tether construction, the distal end surface of the proximal portion of the snare structure has a hole or dimple dimensioned to be about 0.100" deep and approximately 0.017" in diameter. This hole receives the end of the snare loop, which is ultimately crimped into place. The snare loop is made of nitinol stranded wire having a diameter of approximately 0.006". The length of stranded wire is approximately 0.400", which when crimped provides a loop of approximately 0.100" in length.

The pin wire preferably is a nitinol wire having a diameter of approximately 0.017" and a length of approximately 47.25".

While a preferred embodiment of the present invention has been described, it should be understood that various changes, adaptations and modifications may be made therein without departing from the spirit of the invention. Changes may be made in details, particularly in matters of shape, size, material, and arrangement of parts without exceeding the scope of the invention. Accordingly, the scope of the invention is as defined in the language of the appended claims.

What is claimed is:

1. A method for closing an opening in a patient, comprising:

providing a delivery catheter having a lumen extending therethrough;

providing a closure device configured for collapsible containment within the lumen, the closure device having a tether slidably engaged with at least a portion of the device;

providing a snare structure for holding the closure device, the snare structure comprising a loop;

advancing the delivery catheter to the opening;

pushing the closure device out of the lumen for deployment into the opening, the closure device when deployed having a first portion engaging one side of the opening and a second portion engaging a second side of the opening;

holding a portion of the tether with an element at a location proximal to the closure device to limit movement of the tether relative to the closure device; and holding a position of the closure device using the loop of the snare structure;

wherein the closure device may be fully and reversibly deployed while a portion of the tether is being held and the snare structure holds the position of the closure device.

2. The method of claim 1, further comprising liberating the tether from the closure device.

3. The method of claim 2, further comprising removing the delivery catheter from the treatment site and leaving the closure device at the treatment site for closing the opening in the patient.

4. The method of claim 1, wherein the closure device is self-expanding when pushed out of the lumen.

5. The method of claim 1, wherein the snare structure holds the position of the closure device through engagement with the element.

6. The method of claim 1, wherein the opening is located in a septum between left and right atria of the heart.

7. A system for closing a passage between left and right atrial chambers of a heart, the system comprising:
 a closure device configured for preventing the flow of blood between the chambers of the heart;
 a delivery catheter having a delivery lumen extending longitudinally therethrough, the delivery lumen being configured for slidably receiving the closure device;
 a pushing tube slidably disposed within the delivery lumen of the delivery catheter, the pushing tube having at least one inner lumen extending longitudinally therethrough;
 an elongate tether coupled to a portion of the closure device for holding and releasing the closure device;
 an element attachable to the elongate tether for holding the closure device, the element when attached to the elongate tether being at a location proximal to the closure device; and
 a snare structure slidably disposed within the delivery lumen of the delivery catheter, the distal portion of the snare structure comprising a loop, the snare structure configured to hold a position of the closure device using the loop;
 wherein the closure device can be fully and reversibly deployed at the passage while the tether is coupled to the closure device.

8. The system of claim 7, wherein the elongate tether further comprises a proximal end portion and a distal end portion, the distal end portion being releasably coupled to the closure device, the proximal end portion extending from the delivery catheter for allowing reversible deployment of the closure device at the passage.

9. The system of claim 7, wherein the element is releasably attachable to the elongate tether for holding and releasing the closure device.

10. A defect closure device comprising:
 a defect occluder configured to conform to and block a defect;
 a catheter configured to deliver the defect occluder to the defect, the defect occluder being reversibly collapsible within the catheter;
 a tether connected to the defect occluder for reversible free-floating tethered deployment of the defect occluder in the defect;
 a pusher tube having a lumen that receives the tether; and
 a snare structure having a distal portion comprising a snare loop for preventing release of the defect occluder;
 wherein the defect occluder may be fully and reversibly deployed while the loop holds the position of the defect occluder.

11. The defect closure device of claim 10, further comprising an anchor element for anchoring the occluder.

12. The defect closure device of claim 11, wherein the anchor element is connected to the tether.

13. The defect closure device of claim 12, wherein the tether is detachable from the anchor element.

14. The defect closure device of claim 11, wherein the anchor element extends through the pusher tube.

15. The defect closure device of claim 11, wherein the anchor element is a pin wire.

16. The defect closure device of claim 11, wherein the snare loop loops around the anchor element.

17. The defect closure device of claim 10, wherein the defect occluder includes eyelets for receiving suture loops.

18. The defect closure device of claim 10, wherein the defect occluder comprises a first portion and a second portion configured to be positioned on opposite sides of the defect.

19. A method for closing a hole in the septum dividing the left and right atria of the heart, comprising:
 providing a delivery catheter having a lumen extending therethrough;
 providing a closure device configured for collapsible containment within the lumen and a tether slidably engaged with at least a portion of the device;
 providing a pusher tube having a lumen that receives the tether, the pusher tube being receivable in the lumen of the delivery catheter;
 providing a snare structure having a distal portion comprising a snare loop for preventing release of the closure device, the snare structure being receivable in the lumen of the delivery catheter;
 advancing the delivery catheter to the hole with the closure device collapsed within the lumen of the delivery catheter; and
 pushing at least part of the closure device out of the lumen of the delivery catheter into the hole with the snare structure holding the closure device, the closure device having a first portion engaging one side of the hole and a second portion engaging a second side of the hole, the tether maintaining connection with the closure device for reversible free-floating deployment of the closure device in the hole.

20. The method of claim 19, further comprising releasing the snare loop from the closure device to deploy the closure device into its final position.

21. The method of claim 19, further comprising liberating the tether from the closure device.

22. The method of claim 19, wherein the closure device is self-expanding when pushed out of the lumen.

23. The method of claim 19, further comprising providing an anchor element for anchoring the closure device.

24. The method of claim 23, wherein the snare structure prevents release of the closure device by releasably engaging the anchor element.

25. The method of claim 23, further comprising connecting the tether to the anchor element.

26. The method of claim 25, further comprising detaching the tether from the anchor element to deploy the closure device into its final position.

27. The method of claim 19, wherein the closure device includes eyelets for receiving suture loops.

* * * * *

UNITED STATES PATENT AND TRADEMARK OFFICE
CERTIFICATE OF CORRECTION

| | | |
|---|---|---|
| PATENT NO. | : 7,479,155 B2 | Page 1 of 1 |
| APPLICATION NO. | : 10/227773 | |
| DATED | : January 20, 2009 | |
| INVENTOR(S) | : Gainor et al. | |

It is certified that error appears in the above-identified patent and that said Letters Patent is hereby corrected as shown below:

Page 2, Column 2, Line 36, "2001/0049292 A1 12/2001 Frazier, et al." should be changed to --2001/0049492 A1 12/2001 Frazier, et al.--

Signed and Sealed this

Eighteenth Day of August, 2009

David J. Kappos
*Director of the United States Patent and Trademark Office*